(12) United States Patent
Kuhlmann

(10) Patent No.: US 8,291,907 B2
(45) Date of Patent: Oct. 23, 2012

(54) APPARATUS FOR SUPPORTING THE HEAD OF A PERSON LYING PRONE OR ON A SIDE

(76) Inventor: David Charles Kuhlmann, Warsaw, MO (US)

( * ) Notice: Subject to any disclaimer, the term of this patent is extended or adjusted under 35 U.S.C. 154(b) by 991 days.

(21) Appl. No.: 12/246,119

(22) Filed: Oct. 6, 2008

(65) Prior Publication Data

US 2009/0133698 A1    May 28, 2009

Related U.S. Application Data

(60) Provisional application No. 60/979,539, filed on Oct. 12, 2007, provisional application No. 61/082,005, filed on Aug. 1, 2008.

(51) Int. Cl.
*A61M 11/00*    (2006.01)
(52) U.S. Cl. .................. 128/207.11; 128/207.17; 2/410; 2/418
(58) Field of Classification Search ............. 128/207.11, 128/848, 207.13, 207.17, 206.27; 2/171.2, 2/183, 410, 418
See application file for complete search history.

(56) References Cited

U.S. PATENT DOCUMENTS

| | | | |
|---|---|---|---|
| 3,239,843 A * | 3/1966 | Lobelle ............................ | 2/6.4 |
| 4,676,236 A * | 6/1987 | Piorkowski et al. ..... | 128/201.23 |
| 4,989,596 A | 2/1991 | Macris et al. | |
| 5,269,035 A | 12/1993 | Hartunian | |
| 5,584,073 A * | 12/1996 | Radzelovage et al. ............. | 2/6.3 |
| 5,732,414 A * | 3/1998 | Monica ............................. | 2/425 |
| 5,960,494 A | 10/1999 | Gilliland et al. | |
| 6,230,350 B1 | 5/2001 | Goldstein | |
| 6,279,172 B1 * | 8/2001 | Epperson et al. ................. | 2/410 |
| 6,671,907 B1 | 1/2004 | Zuberi | |
| 6,842,924 B1 | 1/2005 | Walters | |
| 6,886,559 B2 * | 5/2005 | McDonald et al. ...... | 128/201.24 |
| 7,063,085 B2 | 6/2006 | Silva et al. | |
| 7,225,811 B2 | 6/2007 | Ruiz et al. | |
| 7,243,651 B2 | 7/2007 | Kwok et al. | |
| 2006/0137100 A1 | 6/2006 | Barczyk | |
| 2008/0047560 A1 | 2/2008 | Veliss et al. | |

* cited by examiner

*Primary Examiner* — Steven Douglas
(74) *Attorney, Agent, or Firm* — Barnes & Thornburg, LLP

(57) ABSTRACT

An apparatus for supporting the head of a person lying prone or on a side includes a base member that is configured to be worn on the head of the person and to rotate between a plurality of positions relative to a support surface upon which the base member rests. The base member defines at least one support member configured to contact the face of the person. A front support structure is mounted to the base member. The front support structure and the base member are cooperatively arranged to define a space between the front support structure and the face of the person wearing the apparatus. The at least one support member is configured to support the head of the person away from the front support structure when the person is lying prone or on a side and with the base member in any of the plurality of positions.

20 Claims, 12 Drawing Sheets

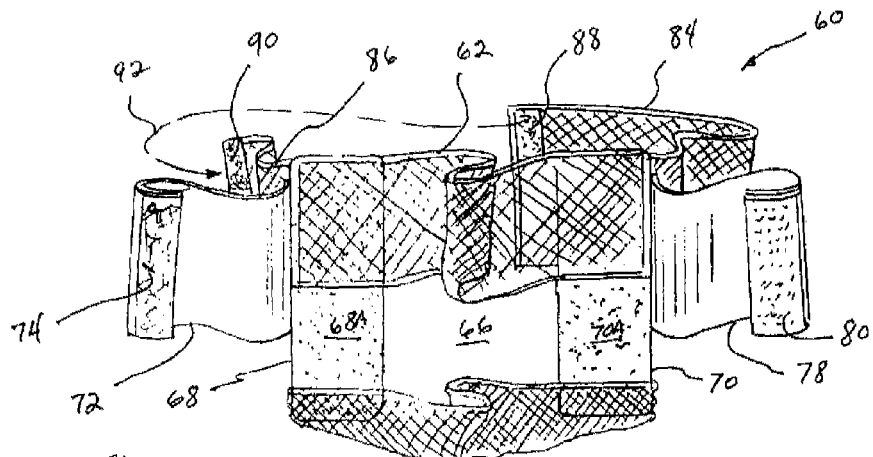
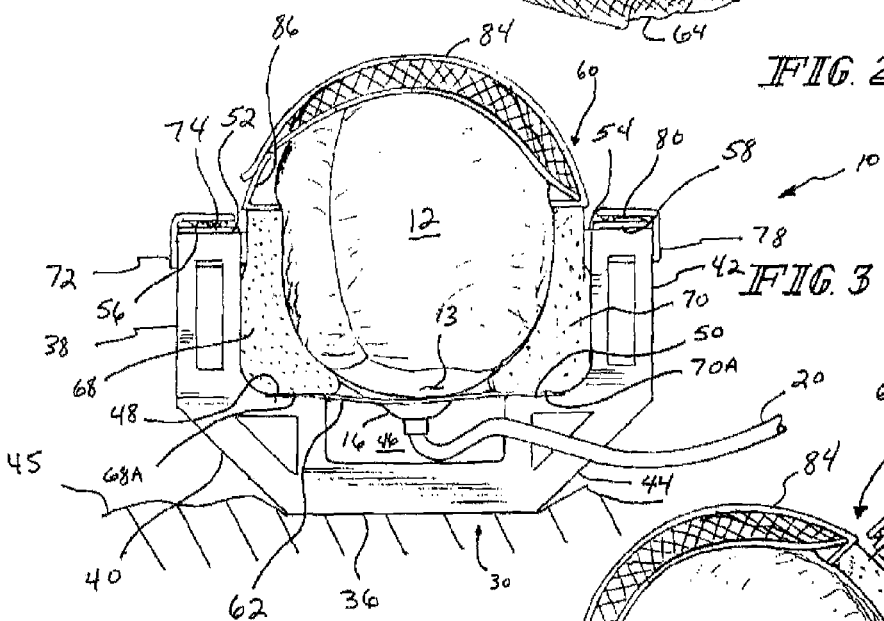
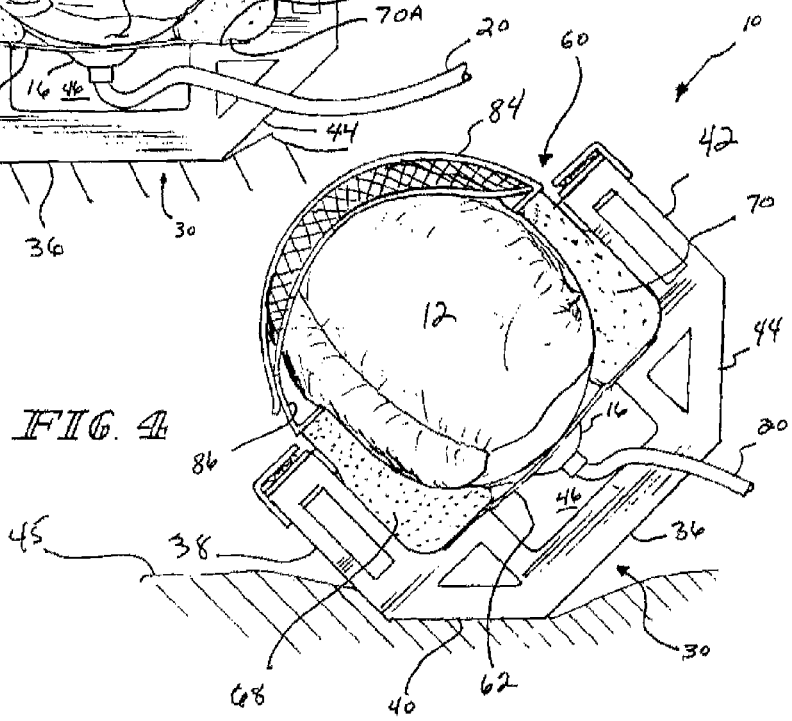
FIG. 2
FIG. 3
FIG. 4

APPARATUS FOR SUPPORTING THE HEAD OF A PERSON LYING PRONE OR ON A SIDE

CROSS-REFERENCE TO RELATED APPLICATIONS

This application claims priority to Provisional Patent Application Ser No. 60/979,539 filed Oct. 12, 2007 and to Provisional Patent Application Ser. No. 61/082,005, filed Jul. 18, 2008, the disclosures of which are both incorporated herein by reference.

FIELD OF THE INVENTION

The present invention relates generally to the fields of sleep therapy, anesthesiology, post surgical care and medical treatment generally, and more specifically to an apparatus for supporting the head of a person lying prone or on a side.

BACKGROUND

It may be desirable for some persons suffering from an obstructive sleep disorder or other disorder or condition to lie fully prone, i.e., face down. It may be alternatively or additionally desirable for persons wearing a breathing assist device to be able to lie fully prone or to lie prone with the head partially or fully to one side. It is desirable to provide support for the head of any such persons that allows the person to rest in a fully prone position or in a prone position with the head partially or fully to one side.

SUMMARY

The present invention may comprise one or more of the features recited in the attached claims, and/or one or more of the following features and combinations thereof. An apparatus for supporting the head of a person lying prone or on a side and wearing a mask of a breathing assist device may comprise a base member, and a flexible support member. The flexible support member may define an opening and may be configured to receive at least a portion of a face of the person with at least part of the mask extending into the opening. The flexible support member may further be configured to be mounted to the base member such that the support member and the base member cooperate to support the head of the person with at least part of the mask positioned between the support member and the base member when the person is lying prone or on a side.

The base member may be rotatable relative to a support surface upon which the base member rests. A longitudinal axis may be defined through the head of the person. The base member may be rotatable in directions perpendicular to the longitudinal axis.

The base member may define a number of different discrete positions relative to the support surface. The base member may be rotatable relative to the support surface between the number of discrete positions. Alternatively, the base member may be continuously rotatable relative to the support surface.

The base member may define a convex outer surface and a concave inner surface. The flexible support member may be configured to be mounted to the base member such that the head of the person is at least partially received within the concave inner surface with the at least part of the mask extending further into the concave inner surface.

The breathing assist device may comprise a gas line having one end fluidly connected to the mask and an opposite end. The base member may define an opening through which the opposite end of the gas line extends externally to the apparatus. The breathing assist device may further comprise a source of gas. The opposite end of the gas line may be configured to be fluidly connectable to the source of gas. The source of gas may be, for example, an air pump. The breathing assist device may comprise one of a continuous positive air pressure (CPAP) device, a two-pressure positive airway pressure (Bi-PAP) device, a variable pressure positive airway pressure (VPAP) device and an automatic positive airway pressure (APAP) device.

The opening defined by the flexible support member may extend through the flexible support member such that the mask extends through the flexible support member.

The mask of the breathing assist device may comprise a nasal mask. The opening defined by the flexible support member may be sized to receive at least part of the nasal mask therein. Alternatively, the mask of the breathing assist device may comprise a face mask configured to cover a nose and mouth of the person. The opening defined by the flexible support member may be sized to receive at least part of the face mask therein.

The flexible support member may comprise a face receiving portion having a forehead support and a chin support with the opening defined between the forehead and chin supports. The forehead support may be configured to receive at least a portion of a forehead of the person and the chin support may be configured to receive at least a portion of a chin of the person with the mask extending into the opening between the forehead support and the chin support. The mask of the breathing assist device may comprise a nasal mask. The forehead support, chin support and opening defined by the flexible support member may all be configured such that the forehead support receives at least a portion of the forehead of the person and the chin support receives at least a portion of the chin of the person with the nasal mask extending into the opening defined by the flexible support member. Alternatively, the mask of the breathing assist device may comprise a face mask configured to cover a nose and mouth of the person. The forehead support, chin support and opening defined by the flexible support member may all be configured such that the forehead support receives at least a portion of the forehead of the person and the chin support receives at least a portion of the chin of the person with the face mask extending into the opening defined by the flexible support member. The forehead support and the chin support may both be formed of a breathable mesh material. The flexible support member may further comprise padding members attached to opposing sides of each of the forehead support and the chin support.

The flexible support member may further comprise at least one securing member configured to extend at least partially about the head of the person and configured to releasably engage one of another securing member of the flexible support member and the flexible support member to thereby restrain movement of the head of the person relative to the apparatus. The at least one securing member may be formed of a breathable mesh material.

The flexible support member may further comprise at least one attachment member configured to be secured to the base member. The flexible support member may be mounted to the base member by securing the at least one attachment member to the base member. The at least one attachment member may comprise two attachment members. One of the two attachment members may be configured to be secured to one side of the base member and the other of the two attachment members is configured to be secured to an opposite side of the base member such that the face of the person is received by the flexible support member between the two attachment members.

The mask may be attached to the flexible support member with the at least part of the mask extending into the opening. Alternatively, the mask may be integral with the flexible support member with the at least part of the mask extending into the opening.

An apparatus for supporting the head of a person lying prone or on a side and wearing a mask of a breathing assist device may comprise a base member configured to rotate between a plurality of positions relative to a support surface upon which the base member rests, and a flexible support member. The flexible support member may define an opening and may be configured to receive at least a portion of a face of the person with at least part of the mask extending into the opening. The flexible support member may be further configured to be mounted to the base member such that the flexible support member and the base member cooperate to support the head of the person when lying prone or on a side and with the base member in any of the plurality of positions.

In one embodiment, the base member may be configured to rotate, relative to the support surface, between at least a first position in which the person is lying prone and the face of the person faces the support surface, a second position in which the head of the person is at least partially turned to one side and a third position in which the head of the person is at least partially turned to an opposite side.

In an alternative embodiment, the base member may be configured to rotate, relative to the support surface, between a first position in which the person is lying prone and the face of the person faces the support surface, a second position in which the head of the person is turned to one side, a third position in between the first and second positions, a fourth position in which the head of the person is turned to an opposite side and a fifth position between the first and fourth positions. In another alternative embodiment, the base member may be configured to smoothly rotate, relative to the support surface, to any position between a first position in which the head of the person is at least partially turned to one side and a second position in which the head of the person is at least partially turned to an opposite side.

The base member may define a convex outer surface and a convex inner surface. The flexible support member may be configured to be mounted to the base member such that the head of the person is at least partially received within the concave inner surface with the at least part of the mask extending further into the concave inner surface.

The breathing assist device may comprise a gas line having one end fluidly connected to the mask and an opposite end. The base member may define an opening through which the opposite end of the gas line extends externally to the apparatus. The breathing assist device may comprise one of a continuous positive air pressure (CPAP) device, a two-pressure positive airway pressure (BiPAP) device, a variable pressure positive airway pressure (VPAP) device and an automatic positive airway pressure (APAP) device.

The mask of the breathing assist device may comprise a nasal mask. The opening defined by the flexible support member may be sized to receive at least part of the nasal mask therein. Alternatively, the mask of the breathing assist device may comprise a face mask configured to cover a nose and mouth of the person. The opening defined by the flexible support member may be sized to receive at least part of the face mask therein.

At least a portion of the flexible support member may be formed of a breathable mesh material.

The flexible support member may further comprise at least one securing member configured to extend at least partially about the head of the person and configured to releasably engage one of another securing member of the flexible support member and the flexible support member to thereby restrain movement of the head of the person relative to the apparatus. The at least one securing member may be formed of a breathable mesh material.

The flexible support member may further comprise at least one attachment member configured to be secured to the base member. The flexible support member may be mounted to the base member by securing the at least one attachment member to the base member. The at least one attachment member comprises two attachment members. One of the two attachment members may be configured to be secured to one side of the base member and the other of the two attachment members may be configured to be secured to an opposite side of the base member such that the face of the person is received by the flexible support member between the two attachment members.

The mask may be attached to the flexible support member with the at least part of the mask extending into the opening. Alternatively, the mask may be integral with the flexible support member with the at least part of the mask extending into the opening.

An apparatus for supporting the head of a person lying prone or on a side may comprise a base member configured to be worn on the head of the person and to rotate between a plurality of positions relative to a support surface upon which the base member rests. The base member may define at least one support member configured to contact the face of the person. A front support structure may be mounted to the base member. The front support structure and the base member may be cooperatively arranged to define a space between the front support structure and the face of the person wearing the apparatus. The at least one support member may be configured to support the head of the person away from the front support structure when the person is lying prone or on a side and with the base member in any of the plurality of positions.

The space defined between the front support structure and the face of the person wearing the apparatus may be sized to provide for adequate ventilation when the person wearing the apparatus is lying fully prone and face-down with the front support structure supported by a support surface. The at least one support member may comprise a forehead support member configured to receive and support at least a portion of a forehead of the person and a chin support member configured to receive and support at least a portion of a chin of the person. The at least one support member may further comprise a first cheek support member connected between the base member and the chin support member and configured to receive and support at least a portion of one cheek of the person, and a second cheek support member connected between the base member and the chin support member and configured to receive and support at least a portion of an opposite cheek of the person. The base member may further comprise a first ear portion connected to the first cheek support member and to the forehead support member, the first ear portion configured to extend at least partially over one ear of the person, and a second ear portion connected to the second cheek support member and to the forehead support member, the second ear portion configured to extend at least partially over an opposite ear of the person. The apparatus may further comprise a securing member configured to extend between the first and second ear portions and to secure the apparatus to the user's head.

The base member may be configured to be worn by a person that is also wearing a breathing assist device. The space defined between the front support structure and the face of the person wearing the apparatus may be sized to receive the breathing assist device therein such that components of the breathing assist device are substantially contained between the face of the user and the front support structure.

The breathing assist device may comprise a mask fluidly connected to one end of a gas line. The base member may define an opening through which the gas line extends externally to the base member. The breathing assist device may further comprise a source of gas. An opposite end of the gas line may be configured to be fluidly connectable to the source of gas. The source of gas may be an air pump.

The mask of the breathing assist device may comprise a nasal mask configured to provide a breathing gas to a nose of the person wearing the breathing assist device. The at least one support member may comprise a forehead support member configured to receive and support at least a portion of a forehead of the person and a chin support member configured to receive and support at least a portion of a chin of the person. The at least one support member may further comprise a first cheek support member connected between the base member and the chin support member and configured to receive and support at least a portion of one cheek of the person, and a second cheek support member connected between the base member and the chin support member and configured to receive and support at least a portion of an opposite cheek of the person.

The mask of the breathing assist device may comprise a face mask configured to provide a breathing gas to a nose and mouth of the person wearing the breathing assist device. The at least one support member may comprise a forehead support member configured to receive and support at least a portion of a forehead of the person, a first cheek support member connected to the base member and configured to receive and support at least a portion of one cheek of the person, and a second cheek support member connected to the base member and configured to receive and support at least a portion of an opposite cheek of the person.

The breathing assist device may comprise one of a continuous positive air pressure (CPAP) device, a two-pressure positive airway pressure (BiPAP) device, a variable pressure positive airway pressure (VPAP) device and an automatic positive airway pressure (APAP) device.

The apparatus may further comprise a securing member configured to secure the base member to the user's head.

The apparatus may further comprise at least one strap attached to the base member and configured to engage the head of the person wearing the apparatus, the at least one strap configured to restrain movement of the apparatus relative to the user's head. The at least one strap may comprise an expandable and contractible material. The at least one strap may comprise a first strap having one end attached to the base member and a second strap having one end attached to the base member, and further comprise a retaining structure configured to releasably engage opposite ends of the first and second straps.

BRIEF DESCRIPTION OF THE DRAWINGS

FIG. 2 is a perspective view of the flexible support member of the apparatus of FIG. 1.

FIG. 3 is a front elevational view of the apparatus of FIG. 1 shown with the head of a person lying in the prone position received within the apparatus and with the apparatus supported by a support surface.

FIG. 4 is a front elevational view similar to FIG. 3 except that the apparatus is rotated relative to the support surface.

DESCRIPTION OF THE ILLUSTRATIVE EMBODIMENTS

Figure 1:
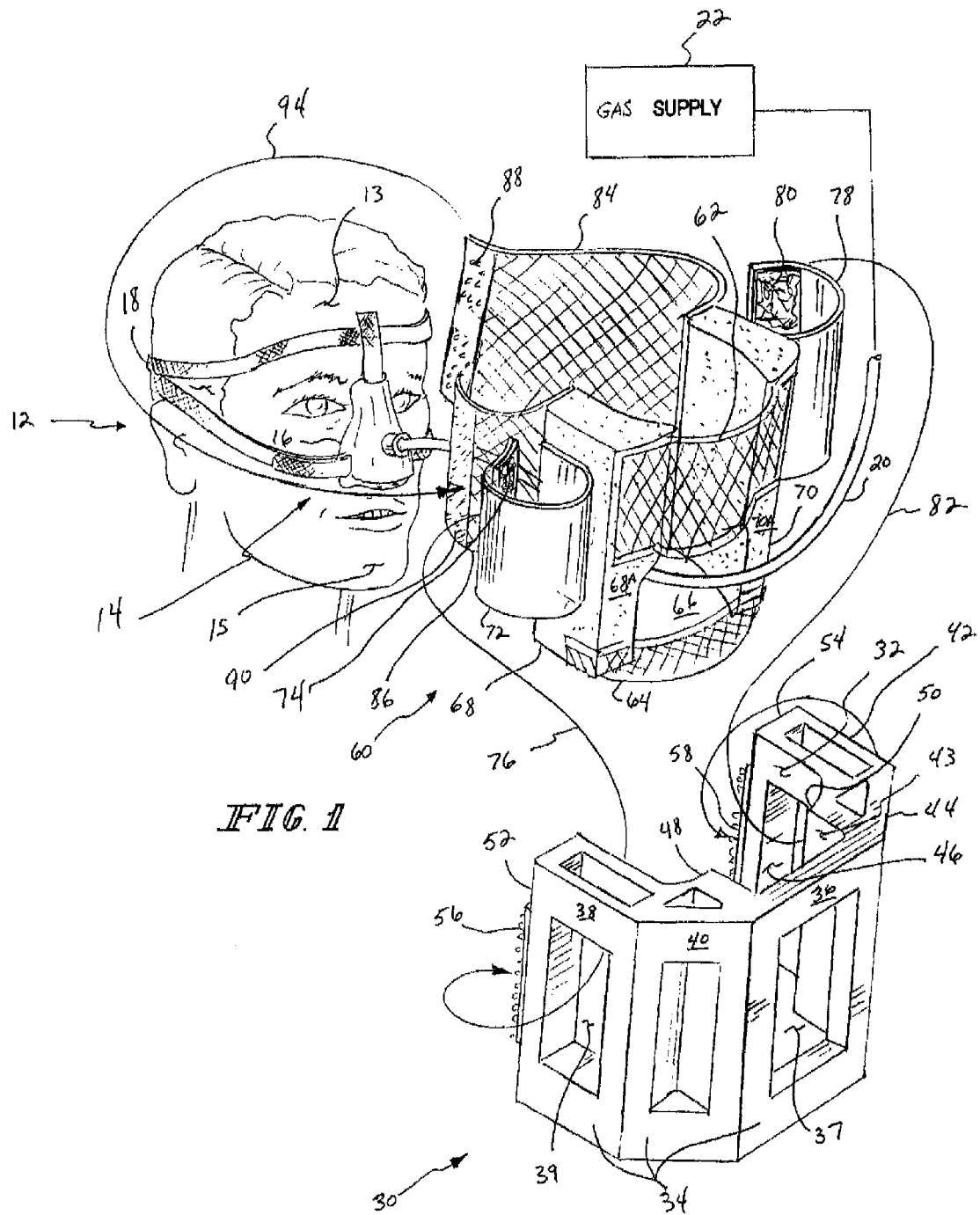
FIG. 1 is an exploded view of an apparatus for supporting the head of a person lying prone or on a side and wearing a mask of a breathing assist device.

For the purposes of promoting an understanding of the principles of the invention, reference will now be made to a number of illustrative embodiments shown in the attached drawings and specific language will be used to describe the same.

Referring now to FIGS. 1-4, various views are shown of an apparatus 10 for supporting the head 12 of a person lying prone or on a side and wearing a mask 16 of a breathing assist device 14. The breathing assist device 14 generally includes an attachment structure 18 for securing the mask 16 to the face of the person. In the illustrated embodiment, for example, the attachment structure 18 includes a strap apparatus that connects at three points to the mask 16 and that extends around the person's head 12. The mask 16, in the illustrated embodiment, is a conventional nasal mask that fits over the nose (not shown) of the person. It will be understood, however, that the mask 16 may alternatively be a conventional face mask that is configured to fit over the mouth of the person and/or the nose of the person, and that the attachment structure 18 may be or include any conventional attachment structure configured to appropriately secure the mask 16 to the person's face. In some alternative embodiments, the mask 16 may be attached to or integral with the apparatus 10 as will be described in greater detail hereinafter, and in such embodiments the attachment structure 18 may or may not be omitted.

In any case, the breathing assist device 14 further includes a source or supply 22 of gas and a gas tube 20 having one end fluidly connected to the mask 16 and an opposite end that is fluidly connectable to the source of gas 22. The breathing assist device is operable in a conventional manner to supply a gas from the source 22 of gas to the internal volume of the mask 16 via the gas tube 20. The person wearing the mask 16 thus receives breathing assistance by breathing the gas supplied by the source of gas 22. In one embodiment, the source 22 of gas is a conventional air pump configured to supply positive pressure air to the mask 16, although the source 22 of gas may alternatively be any conventional source of any conventional gas that provides breathing assistance. Examples of conventional gases and/or vapors that provide breathing assistance may include, but are not limited to, air, oxygen, humidified air or oxygen, one or more conventional medication gases and/or vapors such as one or more anesthetic gases and/or vapors, one or more throat, bronchial airway and/or lung treatment gases and/or vapors, one or more sedation gases and/or vapors, or the like.

In the illustrated embodiment, the breathing assist device 14 is a conventional positive air pressure device that supplies a positive flow of air from the supply 22 to the mask 16 for the purpose of treating one or more sleep disorders, e.g., obstructive sleep apnea (OSA). Examples of such a conventional positive air pressure device include, but should not be limited to, a conventional continuous positive airway pressure (CPAP) device, a conventional two-(bi) pressure positive air pressure (BiPAP) device, a conventional variable-pressure positive airway pressure (VPAP), a conventional automatic positive airway pressure (APAP) device, and the like.

In the embodiment illustrated in FIGS. 1-4, the apparatus 10 includes a base member 30 and a flexible support member 60. Generally, the flexible support member 60 defines an opening 66, and is configured to receive the face of a person with at least part of the mask 16 extending into the opening 66. In the illustrated embodiment, all or most of the mask 16 extends into the opening 66. Illustratively, as shown in FIGS. 1-4, the opening 66 may be defined completely through the flexible support member 60, in which case at least part of the mask 16 extends into the opening 66 and completely through the flexible support member 60, although this disclosure contemplates other embodiments in which the opening 66 extends into, but not completely through, the flexible support member 60, in which case at least a portion of the mask 16 extends into the opening 66 but not completely through the flexible support member 60. In other alternative embodiments, the mask 16 may be integral with or attached, via one or more suitable attachment mechanisms and/or media, to the flexible support member 60 such that at least part of the mask 16 extends through the opening 66. In any case, the flexible support member 60 is configured to be mounted to the base member 30 such that the base member 30 and the flexible support member 60 cooperate to support the head 12 of the person with at least part of the mask 16 positioned between the flexible support member 60 and the base member 30 when the person is lying prone or on one (or the other) side, as most clearly illustrated in FIGS. 3 and 4. The base member 30 is generally configured to rotate, relative to a support surface 45 upon which the base member 30 rests. For example, as most clearly shown in FIG. 4, the base member 30 is configured to rotate, relative to the support surface 45, in directions that are generally perpendicular to a longitudinal axis defined by the person's head 12, e.g., from the top of the person's head through the person's chin 15, so that the person lying prone or on one side (or the other) may move the head 12 at least partially to either side. With the apparatus 10, a person wearing the mask 16 of the breathing assist device 14 may sleep while lying prone or on a side, and may turn his or her head 12 at least partially to one side or the other while sleeping prone or on a side.

In the illustrated embodiment, the base member 30 is shaped such that is has a generally concave inner surface 32 and a generally convex outer surface 34. As most clearly shown in FIGS. 3 and 4, the base member 30 and the flexible support member 60 are configured such that when the flexible support member 60 is mounted to the base member 60 and the person's face engages the flexible support member 60, the head 12 of the person is at least partially received within concave inner surface 32 of the base member 30 with at least part of the mask 16 extending further into the concave inner surface 32. In one embodiment, as illustrated in FIGS. 1, 3 and 4, the convex outer surface 34 of the base member 30 defines a number of different, discrete surfaces or sections that provide for a corresponding number of different positions or orientations of the base member 30 relative to the support surface 45.

In the illustrated embodiment, the convex outer surface 34 of the base member 30 defines five different outer surfaces or sections 36, 38, 40, 42 and 44, and the base member 30 is generally rotatable to any of these outer surfaces 36-44 to thereby position the base member in five corresponding different positions to support the head 12 of the person in a corresponding number of orientations from one side of the head 12 to the other. One such position, as illustrated in FIG. 3, is with the outer surface or section 36 of the base member 30 resting upon the support surface 45. In this position, the face of the person faces the support surface 45 in a generally prone position. Another position, such as illustrated in FIG. 4, is with the outer surface or section 40 of the base member 30 resting upon the support surface 45. In this position, the head 12 of the person is at least partially turned to one side. Yet another position (not illustrated) is with the outer surface or section 38 of the base member 30 resting upon the support surface 45. In this position, the head 12 of the person is fully turned to one side. Two further positions (not illustrated) are with the outer surface or section 44 or 42 of the base member 30 resting upon the support surface 45 such that the head 12 is correspondingly partially or fully turned to the opposite side. The five different surfaces or sections 36-44 of the base member 30 thus provide for five different and discrete positions of the head 12 of the person that range between being fully turned to one side to being fully turned to the opposite side. The body of the person in any of these positions may be in a prone position, lying on one side or the other or any position in between. In this embodiment, the base member 30 defines an opening 46 at the top and bottom thereof, which may be used to provide a routing path for the gas line 20 between the mask 16 and the source of gas 22.

Those skilled in the art will recognize that other configurations of the outer, convex surface 34 of the base member may include more or fewer different, discrete surfaces or sections that provide for a corresponding number of different positions or orientations of the base member 30 relative to the support surface 45. One specific example is an embodiment that includes only three such surfaces or sections that allows positioning of the head 12 of the person between being fully on one side or the other or facing the support surface 45. In any case, one or more of the different, discrete surfaces or sections may define one or more openings between the outer, convex surface 34 and the inner, concave surface 32 to provide for air flow to the inner, concave surface 32 and/or to provide one or more passageways for routing the gas line 20 from the mask 16 to the external gas supply 22.

Alternatively, the outer, convex surface 34 of the base member 30 may be rounded to form a smooth or semi-smooth, continuous or nearly-continuous outer surface 34 so that the base member 30 may be continuously rotatable relative to the support surface 45. For purposes of this document, the term "continuously rotatable" is defined as describing an outer convex surface 34 of the base member 30 that does not define different, discrete positions of the base member 30 relative to the support surface 45, but that rather defines a smooth or semi-smooth outer, convex surface 34 that is generally rotatable between a potentially infinite number of positions between one side and the other. Illustratively, the convex outer surface 34 may, in such embodiments, be or resemble more of a smooth U-shape or other generally parabolic shape. In such embodiments, the base member 30 may define a number of air holes therethrough for ventilation and/or routing of the gas line 20.

Illustratively, the base member 30, regardless of its configuration, is formed from a light weight, low-density rigid or semi-rigid material. In embodiments wherein the base member 30 is formed of a semi-rigid material, it is desirable to use a resilient material so that the base member 30 retains its general shape.

As briefly described hereinabove, the flexible support member 60 defines an opening 66 into which at least part of the mask 16 extends when the flexible support member 60 receives the face of the person. In the illustrated embodiment, the flexible support member 66 has a face receiving portion that includes a forehead support member 62 and a chin support member 64, and the opening 66 is defined between the forehead support member 62 and the chin support member 64. In embodiments in which the mask 16 is a conventional nasal mask, as described hereinabove, the forehead support member 62, the chin support member 64 and the opening 66 are configured and sized such that the forehead support member 62 receives and supports at least a portion of the person's forehead 13, the chin support member 64 receives and supports at least a portion of the person's chin 15, and at least a portion of the nasal mask 16 extends into the opening 66. In the illustrated embodiment, for example, all or most of the nasal mask 16 extends into the opening 66. Likewise, in embodiments in which the mask 16 is a conventional face mask configured to cover the mouth or the combination of the nose and mouth, of the person, the forehead support member 62, the chin support member 64 and the opening 66 are configured and sized such that the forehead support member 62 receives and supports at least a portion of the person's forehead 13, the chin support member 64 receives and supports at least a portion of the person's chin 15, and at least a portion of the face mask 16 extends into the opening 66. In one embodiment, for example, all or most of the face mask 16 extends into the opening 66. In one embodiment, the forehead support member 62 and the chin support member 64 are formed of a conventional breathable mesh material. Alternatively or additionally, the forehead support member 62 and/or the chin support member 64 may be formed of a conventional stretchable material.

The flexible support member 60 further includes padding members 68 and 70 attached to opposing ends of the forehead support member 62 and the chin support member 64. The padding members 68 and 70 are illustratively formed of a conventional compressible foam material, although either or both of the padding members 68 and 70 may alternatively be formed of or include other conventional padding materials, examples of which include, but should not be limited to, memory foam, breathable padding material, polystyrene, an inflatable bladder, or the like. In any case, the padding members 68 and 70 may additionally be configured to include openings, recesses, channels or the like (not shown) to accommodate the ears of the person using the apparatus 10. Any such openings, recesses, channels or the like may be formed partially into or completely through the padding members 68 and 70.

The flexible support member 60 further includes a securing member 84 having one end attached to the padding member 70 and an opposite free end, and another securing member 86 having one end attached to the padding member 68 and an opposite free end. An engagement structure 88 is attached to the free end of the securing member 84, and a complementarily configured engagement structure 90 is attached to the free end of the securing member 84. The engagement structures 88 and 90 are configured to releasably engage each other, and are illustratively provided in the form of conventional hook and loop strips. It will be understood, however, that this disclosure contemplates alternative embodiments in which the engagement structures 88 and 90 are provided in the form of one or more other conventional engagement structures. In any case, the securing member 84 is configured to extend at least partially about the head 12 of the person, as illustrated by the directional arrow 94 in FIG. 1, and releasably engage the securing member 86 via the engagement structures 88 and 90 to thereby restrain movement of the head 12 of the person relative to the apparatus 10 as illustrated most clearly in FIGS. 3 and 4. Illustratively, the securing members 84 and 84 are formed of a breathable mesh material, although this disclosure contemplates that the securing members 84 and 86 may alternatively be formed of or include one or more other conventional materials.

In alternative embodiments, the flexible support member 60 may include more or fewer, i.e., at least one, securing members. Any of the one or more such securing members may be configured to releasably engage another securing member and/or to releasably engage one or more other parts of the flexible support member 60 and/or to releasably engage the base member 30 using any conventional releasable engagement structure(s) and/or technique(s).

The flexible support member 60 further includes an attachment member 72 having one end attached to the foam member 68 and an opposite free end, and another attachment member 78 having one end attached to the foam member 70 and an opposite free end. An engagement structure 74 is attached to the free end of the attachment member 72, and a complementarily configured engagement structure 56 is attached to a top surface 52 of one side of the base member 30. Another engagement structure 80 is attached to the free end of the attachment member 78, and a complementarily configured engagement structure 58 is attached to a top surface 54 of the opposite side of the base member 30. The engagement structures 74 and 56 are configured to releasably engage each other, and the engagement structures 80 and 58 are likewise configured to releasably engage each other. Both sets of engagement structures 74/56 and 80/58 are illustratively provided in the form of conventional hook and loop strips, although this disclosure contemplates alternative embodiments in which the engagement structures 74/56 and 80/58 are provided in the form of one or more other conventional engagement structures. In any case, the attachment member 72 is configured to extend through the opening 39 of the base member 30 and releasably engage the engagement structure 56 via the engagement structure 74 as illustrated by the assembly arrow 76 in FIG. 1. Likewise, the attachment member 78 is configured to extend through the opening 44 of the base member 30 and releasably engage the engagement structure 58 via the engagement structure 80 as illustrated by the assembly arrow 82 in FIG. 1.

With the flexible support member 60 mounted to the base member 30 by securing the attachment members 72 and 78 to the base member 30 as just described, the flexible support member 60 is at least partially suspended within the base member 30. As most clearly illustrated in FIGS. 3 and 4, for example, the base member 30 in the illustrated embodiment includes two support surfaces 48 and 50 that receive the bottom surfaces 68A and 70A respectively of the padding members 68 and 70 respectively. The forehead support member 62 and the chin support member 64 extending between the support surfaces 48 and 50 are suspended above the section 36 of the base member to define the opening 46. In alternative embodiments, the support surfaces 48 and 50 are omitted, and with the flexible support member 60 mounted to the base member 30 by securing the attachment members 72 and 78 to the base member 30 as just described, the flexible support member 60 in this embodiment is fully and completely suspended within the base member 30. Illustratively, the attachment members 72 and 78 are formed of a flexible material, although this disclosure contemplates that the securing members 72 and 78 may alternatively be formed of or include one or more other conventional materials.

In alternative embodiments, the flexible support member 60 may include more or fewer, i.e., at least one, attachment members. Any of the one or more such attachment members may be configured to releasably engage another attachment member and/or to releasably engage one or more parts of the flexible support member 60 and/or to releasably engage one or more other parts of the base member 30 using any conventional releasable engagement or attachment structure(s) and/or technique(s). In the embodiment illustrated in FIGS. 1-4, and with particular reference to FIG. 3, the sections 38 and 42 of the base member 30 may be alternatively configured to extend further upwardly. Alternatively or additionally, the engagement structures 56 and 58 may be located closer to the sections 40 and 44 respectively so that the head 12 of the person extends fully into the base member 30.

Figure 5:
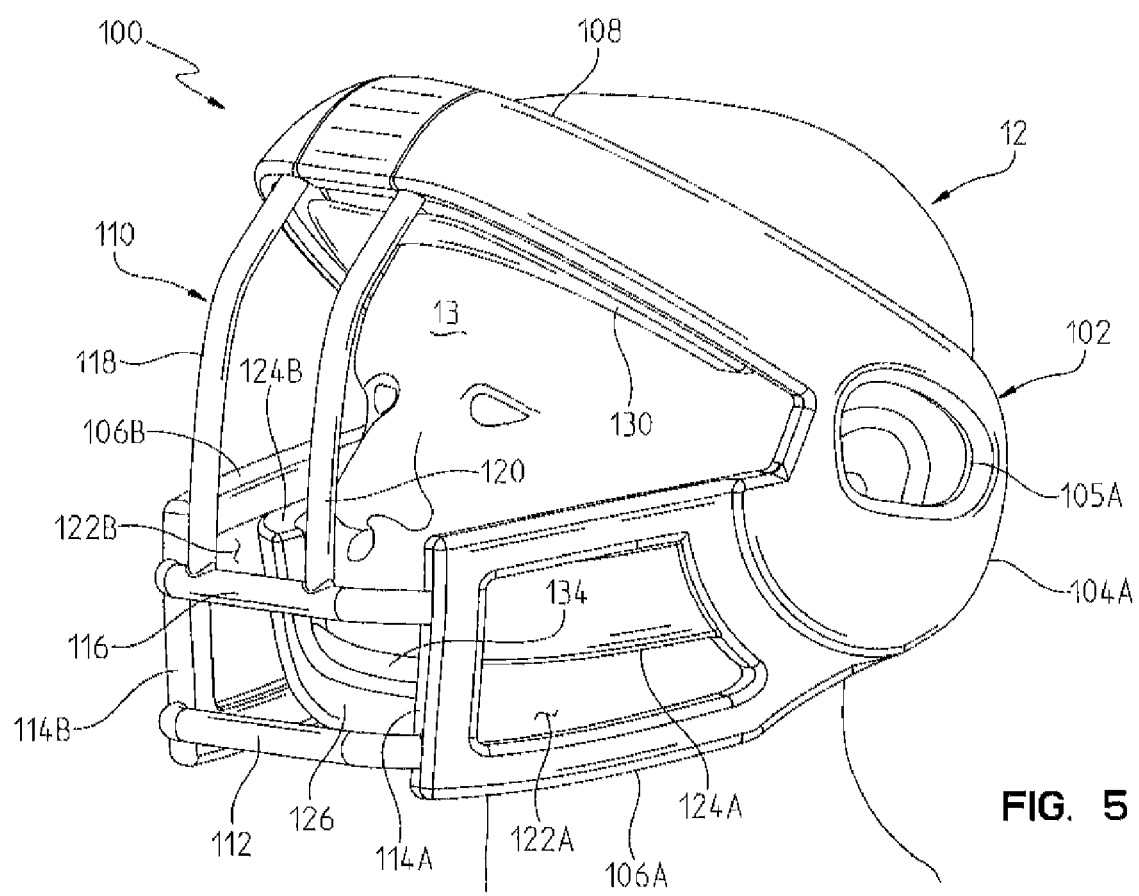
FIG. 5 is a perspective view of another illustrative embodiment of an apparatus for supporting the head of a person lying prone or on a side.
Figure 6:
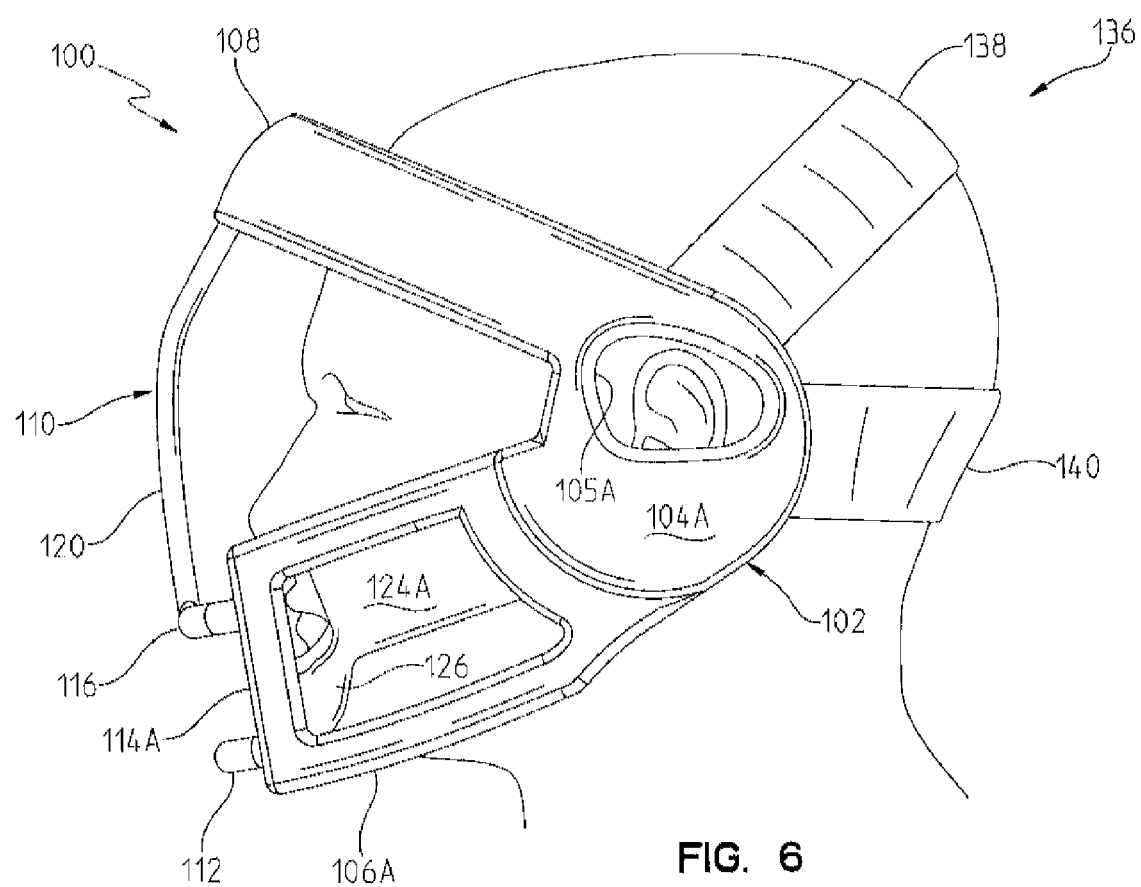
FIG. 6 is a side elevation view of the embodiment illustrated in FIG. 5.
Figure 7:
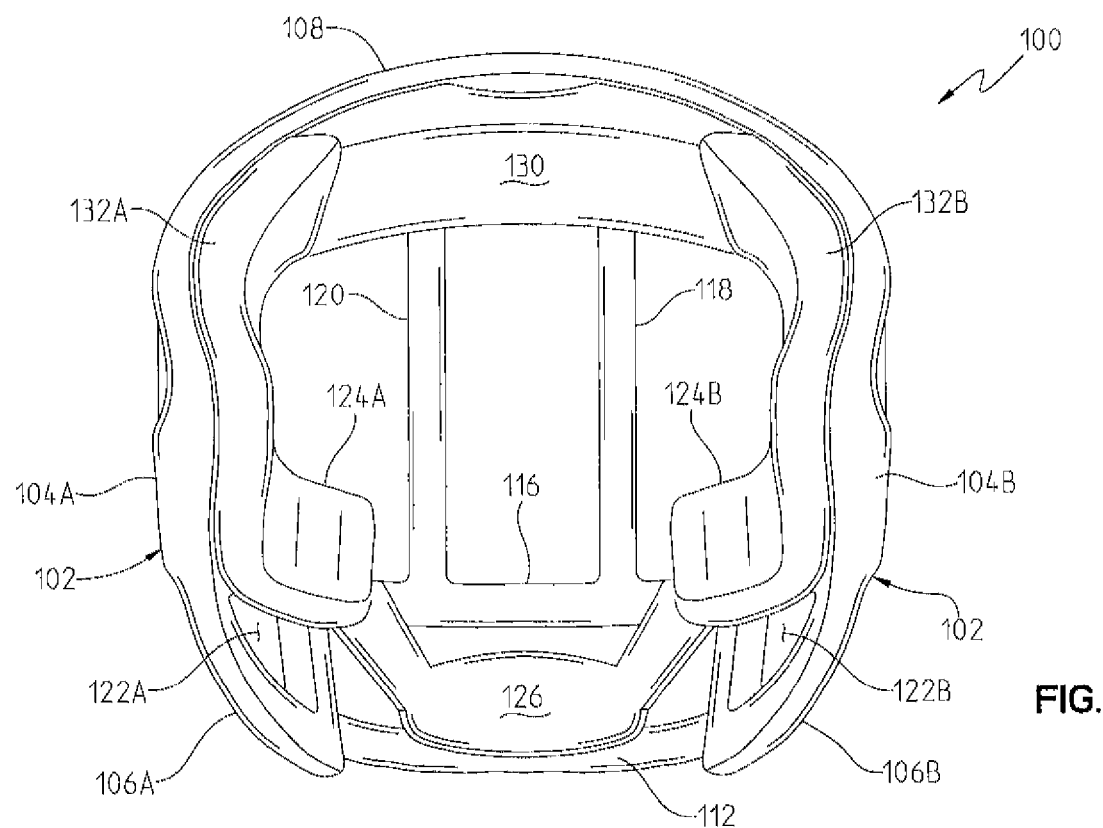
FIG. 7 is a rear view of the embodiment illustrated in FIGS. 5 and 6 showing features internal to the illustrated apparatus.

Referring now to FIGS. 5-7 one alternative embodiment of an apparatus 100 for supporting the head 12 of a person lying prone or on a side is shown. In the illustrated embodiment, the apparatus 100 is intended for use without a breathing assist device, e.g., a breathing assist device 14. In this embodiment, the apparatus 100 is configured to allow a person to sleep in a fully prone position with the head 12 face-down on a support surface, and/or to allow the person to sleep on either side or back with the head 12 in any conventional sleep position. It is believed that by sleeping in the fully prone position, the person's tongue, throat muscles and/or facial muscles will tend to relax outwardly from the person's head 12, thereby removing or lessening breathing obstruction during sleep. The apparatus 100 may accordingly be used by persons having obstructive sleep apnea (OSA) that is not or not yet severe enough to require the use of a breathing assist device, by persons that cannot use a breathing assist device for whatever reason and/or by any persons for one or more different reasons. In any case, the apparatus 100 illustrated in FIGS. 5-7 include a base member 102 that is configured to be worn on and about a person's head 12. The base member 102 is illustratively formed of a rigid or semi-rigid, lightweight material such as polycarbonate, although other and/or additional materials may alternatively be used.

In the illustrated embodiment, the base member 102 of the apparatus 100 includes a pair of rear portions 104A, 104B from which side members 106A and 106B respectively extend. A forehead member 108 extends between and joins each of the rear portions 104A and 104B. The rear portions 104A is configured to extend over and about the person's left ear 17 and the rear portion 104B is configured to extend over and about the person's right ear (not shown). Illustratively, the rear portion 104A defines an opening 105A therethrough that is positioned relative to the base member 102 to align with the left ear 17 of the person wearing the apparatus 100. Likewise, the rear portion 104B illustratively defines an opening (not shown) that is positioned over the right ear of the person wearing the apparatus 100. In some embodiments, the openings 105A may alternatively be omitted. The base member 102 is configured to rotate between a plurality of positions relative to a support surface upon which the base member 102 rests, i.e., the user, when wearing the base member 102, may rotate the head 12 between a plurality of positions, e.g., any position about a 360 degree periphery of the head 12, relative to the support surface upon which the base member 102 rests.

The side members 106A, 106B extend generally from the corresponding rear portion 104A, 104B outwardly alongside the face of the person wearing the apparatus 100, e.g., along the jaw line of the person, and terminate at free ends 114A, 114B thereof. Illustratively, the side members 106A, 106B each define an opening 122A, 122B therethrough. In the illustrated embodiment, the openings 122A, 122B are sized such that the remainder of the side members 106A, 106B generally define a skeletal framework about the openings 122A, 122B. In alternative embodiments, the openings 122A, 122B may be sized smaller than illustrated, may be provided in the form of multiple openings on either or both of the side members 106A, 106B, or may be omitted altogether.

The apparatus 100 further includes a front support structure 110 that is attached to the base member 102 and that extends generally in front of the face of the person wearing the apparatus 100. In the embodiment illustrated in FIGS. 5-7, the front support structure 110 and the base member 102 are cooperatively arranged to provide a space between the front support structure 110 and the face of the person wearing the apparatus 100 that is sized to provide for adequate ventilation, e.g. for normal breathing, when the person wearing the apparatus 100 is lying fully prone and face-down with the front support structure 110 supported by a support surface, e.g., the surface upon which the person is lying such as a conventional mattress or the like. In the illustrated embodiment, the front support structure 110 includes a pair of spaced-apart and generally parallel support bars or tubes 112 and 116 each having one end attached to or integral with the free end 114A of the side member 106A and an opposite end attached to or integral with the free end 114B of the side member 106B. The front support member 110 illustratively includes another pair of spaced apart and generally parallel support bars or tubes 118 and 120 each having one end attached to or integral with the support bar or tube 116 and an opposite end attached to or integral with the forehead member 108. In the illustrated embodiment, the support bars or tubes 118 and 120 extend generally longitudinally along either side of the nose of the person wearing the apparatus 100, and the support bars or tubes 112 and 116 extend generally laterally above and below the mouth of the person wearing the apparatus 100. In one embodiment, the support bars or tubes 112, 116, 118 and 120 are formed from a suitable lightweight metal or metal compound, although one or more of the support bars or tubes may alternatively be formed of other suitable materials including, but not limited to, polycarbonate, graphite, and the like, and/or may be coated or otherwise enveloped with a suitable plastic, rubber, nylon, etc. material. In alternative embodiments, the front support member 110 may be formed from more or fewer bars or tubes, and the bars or tubes in any embodiment may have any desired shape and/or cross-sectional profile, e.g., circular, oval, rectangular, hexagonal, octagonal, etc.

In the illustrated embodiment, the base member 102 of the apparatus 100 further includes a chin and face support member 125. Illustratively, the chin and face support member 125 includes a pair of face support members 124A and 124B each having one end that is attached to or integral with the rear portion 104A, 104B respectively of the base member 102, and an opposite end that is attached to or integral with a chin support member 126. Illustratively, each of the face support members 124A and 124B extend alongside the corresponding side members 106A and 106B and inwardly from the corresponding side members 106A and 106B toward the face of the person wearing the apparatus 100. In the illustrated embodiment, the face support members 124A and 124B contact the face of the person wearing the apparatus 100 at or just under the person's zygomatic (cheek) bones. In the embodiment illustrated in FIGS. 5-7, the user's head 12 is thus supported, when the user is wearing the apparatus 100 and lying prone, by the forehead member 108, the side members 104A, 104B, the face support members 124A, 124B and the chin support member 126.

In alternative embodiments, either or both of the face support members 124A, 124B may include multiple support members, and in any embodiment the face support members may alternatively contact and support the face of the person wearing the apparatus 100 at one or more other locations or positions in addition to or other than at or just under the person's zygomatic bones. In some alternative embodiments, the chin support member 126 may be omitted, and the chin and face support member 125 in such embodiments will include only the face support members 124A and 124B, which may each include one or more face support structures.

The apparatus 100 further includes a number of pads or cushions that are attached to some of the structures of the apparatus 100 and that act as cushioning interfaces between the apparatus 100 and the head/face of the person wearing the apparatus 100. For example, a forehead pad or cushion 130 is mounted to at least a portion of the inside surface of the forehead member 108 and acts as a cushioning interface between the forehead member 108 and the forehead 13 of the person wearing the apparatus 100. As another example, head/face pads or cushions 132A, 132B are mounted to at least portions of the inside surface of corresponding face support members 124A, 124B and to at least portions of the inside surface of corresponding rear portions 104A, 104B, and the pads or cushions 132A, 132B act as cushioning interfaces between the face support and rear portions 124A, 104A and 124B, 104B respectively of the apparatus 100 and the head/face of the person wearing the apparatus 100. As a further example, a chin pad or cushion 134 is mounted to at least a portion of the inside surface of the chin support member 126 and acts as a cushioning interface between the chin support member 126 and the chin 15 of the person wearing the apparatus 100. In one embodiment, the pads or cushions 130, 132A, 132B, 134 are provided in the form of conventional gel packs that are removably mounted to the apparatus. Illustratively, the gel packs may be configured to be artificially cooled or heated, e.g., via a conventional refrigerator or microwave oven. In one alternative embodiment, the pads or cushions 130, 132A, 132B, 134 may be or include conventional breathable material that comes into contact with the head/face/chin of the person wearing the apparatus 100 to minimize or at least reduce moisture resulting from face/head/chin perspiration.

The apparatus 100 further includes a securing member 136 that is attached to the apparatus 100, e.g., that is attached to the rear portions 104A and 104B. The securing member 136 is configured to secure the apparatus 100 to the user's head 12 and to restrain movement of the apparatus 100 relative to the user's head 12. In the illustrated embodiment, the securing member 136 includes a pair of straps or webs 138 and 140 that are each attached to the rear portions 104A, 104B. Illustratively, the strap or web 138 is configured to extend over the top/rear portion of the person's head and the strap or web 140 is configured to extend about the person's head at or near the base thereof. Alternatively, the securing member 136 may include more or fewer such straps or webs 138, 140. In one embodiment, the straps or webs, e.g., 138, 140, are provided in the form of a conventional expandable and contractible material that stretches or otherwise elongates to allow the person to adorn the apparatus 100 and position the straps or webs, e.g., 138 and 140, as illustrated in FIG. 6, and that then automatically shortens or shrinks to secure the apparatus 100 to the person's head/face and restrain movement of the apparatus 100 relative to the person's head/face.

Figure 14A:
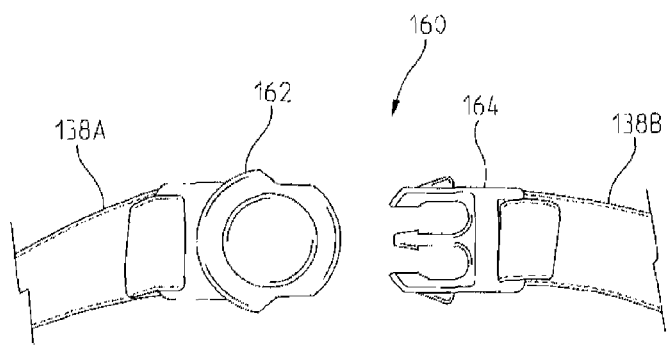
FIGS. 14A and 14B are elevational views of one illustrative embodiment of a retaining structure of a securing device for securing the apparatus to the head of a user.
Figure 14B:
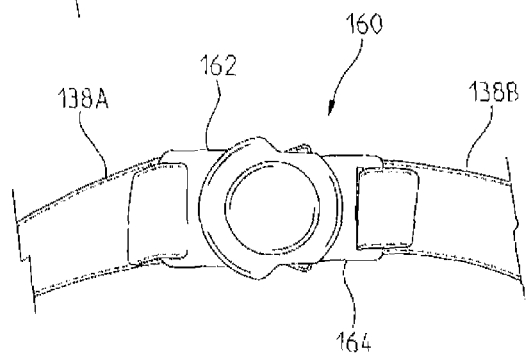

In alternative embodiments, the securing member 136 may include one or more retaining structures that releasably engage each other to secure the apparatus 100 to the head of the person and to allow removal of the apparatus 100 from the head of the person. An example of one such retaining structure 160 is illustrated in FIGS. 14A and 14B. In the illustrated embodiment, the retaining structure 160 is illustrated as being incorporated in the strap or web 138, although it should be understood that the retaining structure 160 may also be incorporated into the strap or web 140. In any case, the strap or web 138 is illustrated as being provided in two sections 138A and 138B, each of which have a different portion 162 and 164 respectively of the retaining structure 160 attached thereto. In the illustrated embodiment, the retaining structure 160 is provided in the form of conventional locking portions 162, 164 that are configured to releasably engage each other in a conventional manner. In alternative embodiments, the retaining structure 160 may be provided of other conventional forms including, but not limited to, one or more hook and loop engageable members, tongue and buckle members, or the like. In any case, the retaining structure 160 will generally be configured to allow the securing member 136 to be adjustably fitted to the user's head.

Figure 8:
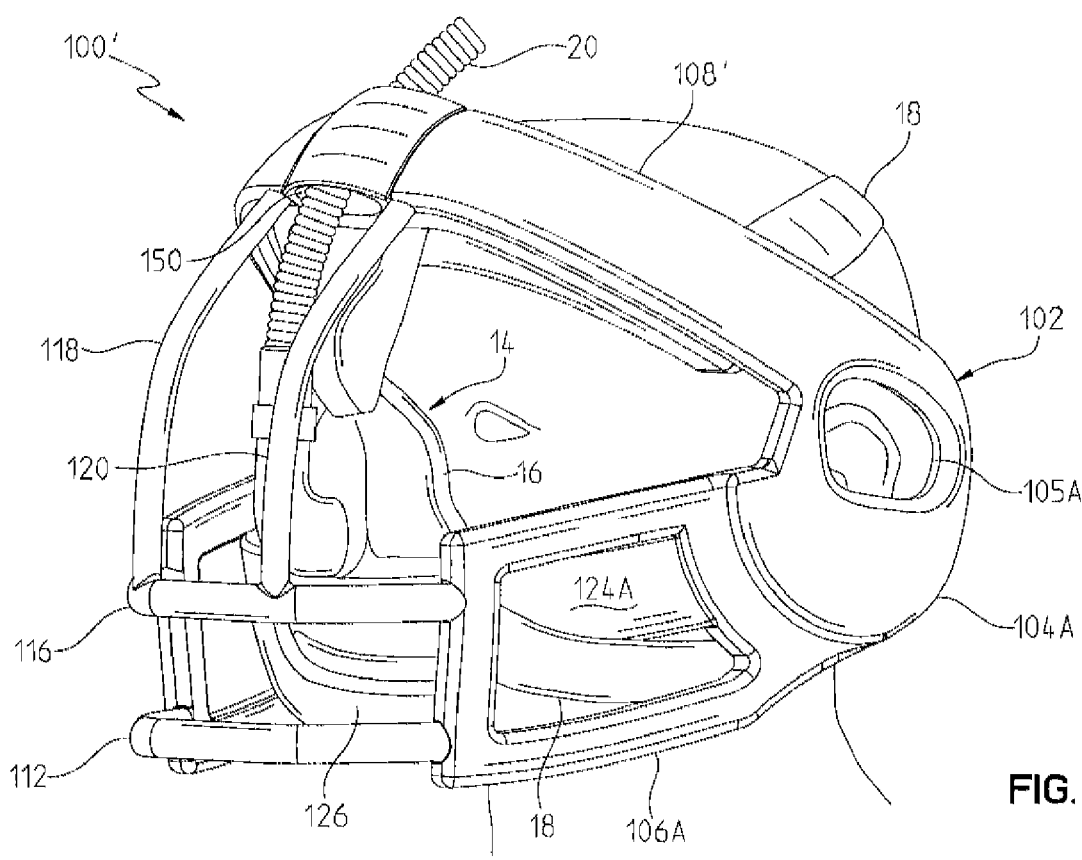
FIG. 8 is a perspective view of yet another illustrative embodiment of an apparatus for supporting the head of a person lying prone or on a side and wearing a breathing assist device.
Figure 9:
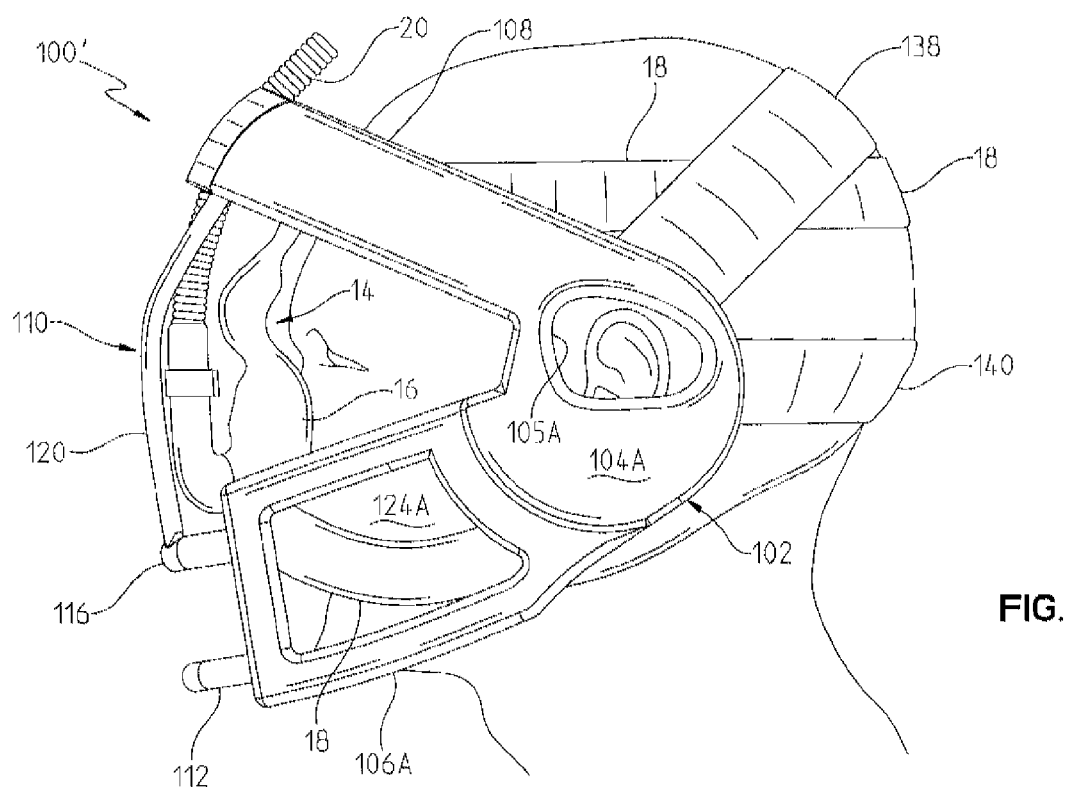
FIG. 9 is a side elevation view of the embodiment illustrated in FIG. 8.
Figure 10:
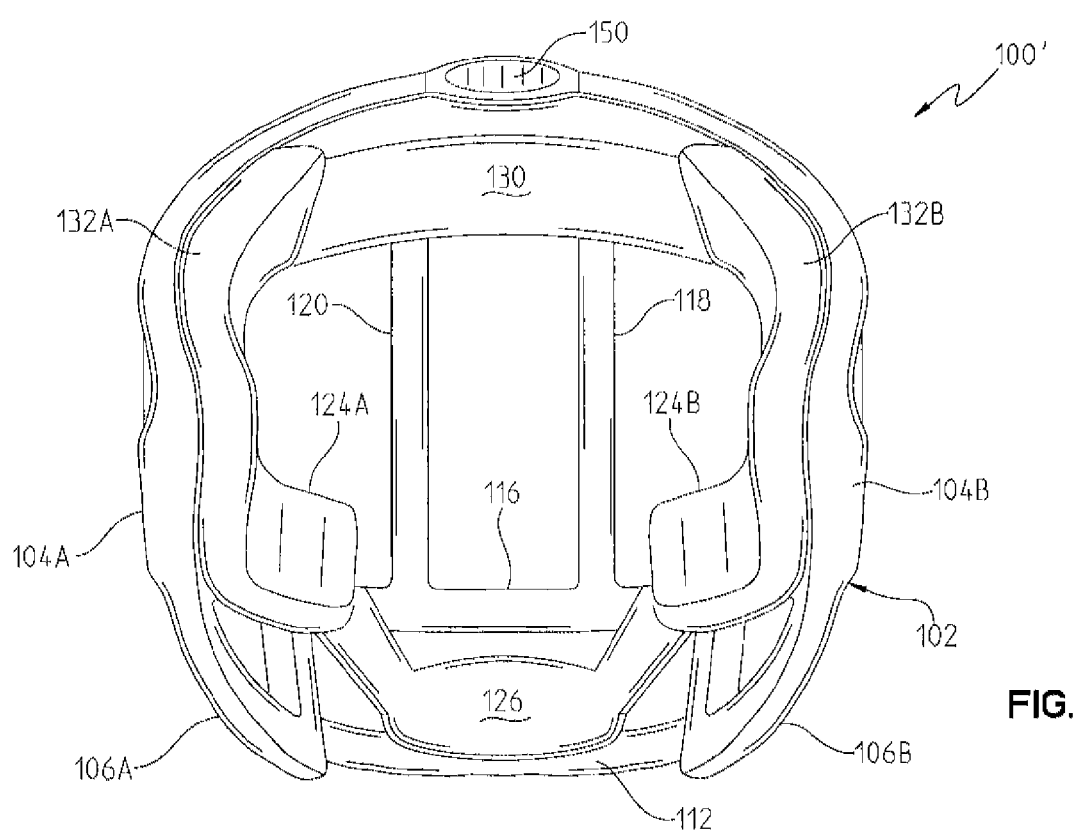
FIG. 10 is a rear view of the embodiment illustrated in FIGS. 8 and 9 showing features internal to the illustrated apparatus.

Referring now to FIGS. 8-10, another alternative embodiment of an apparatus 100' for supporting the head 12 of a person lying prone or on a side is shown. The apparatus 100' is identical in may respect to the apparatus 100 illustrated and described with respect to FIGS. 5-7, and like numbers are therefore used to identify like components. In the illustrated embodiment, the apparatus 100' differs from the apparatus 100 in that the apparatus 100' is intended specifically for use with a nasal-type breathing assist device 14 of the type illustrated and described hereinabove with respect to FIGS. 1-4, i.e., the type of breathing assist device 14 having a mask 16 that fits generally over, and supplies a breathing gas to, the user's nose. In this regard, the forehead member 108' defines a passageway 150 that is sized to receive therethrough the gas line 20 that connects the breathing assist device 20 to the gas supply 22 (not shown in FIGS. 8-10). Also in the embodiment illustrated in FIGS. 8-10, the front support structure 110 and the base member 102 are cooperatively arranged to provide a space between the front support structure 110 and the face of the person wearing the apparatus 100 that is sized to receive the breathing assist device 14 therein such that the various components of the breathing assist device 14, when being worn by the user 12, are contained between the face of the user 12 and the front support structure 110, i.e., such that none of the various components of the breathing assist device 14 extend beyond the front support structure 110. This allows the person wearing the breathing assist device 14 and the apparatus 100' to lie fully prone and face-down with the front support structure 110 supported by a support surface, e.g., the surface upon which the person is lying, such as a conventional mattress or the like. In the embodiment illustrated in FIGS. 8-10, the user's head 12 is supported, when the user is wearing the apparatus 100 and lying prone, by the forehead member 108, the side members 104A, 104B, the face support members 124A, 124B and the chin support member 126. It will be understood that the various alternative structures and/or omissions described above with respect to the apparatus 100 illustrated and described with respect to FIGS. 5-7 are also applicable to the apparatus 100' illustrated in FIGS. 8-10.

Figure 11:
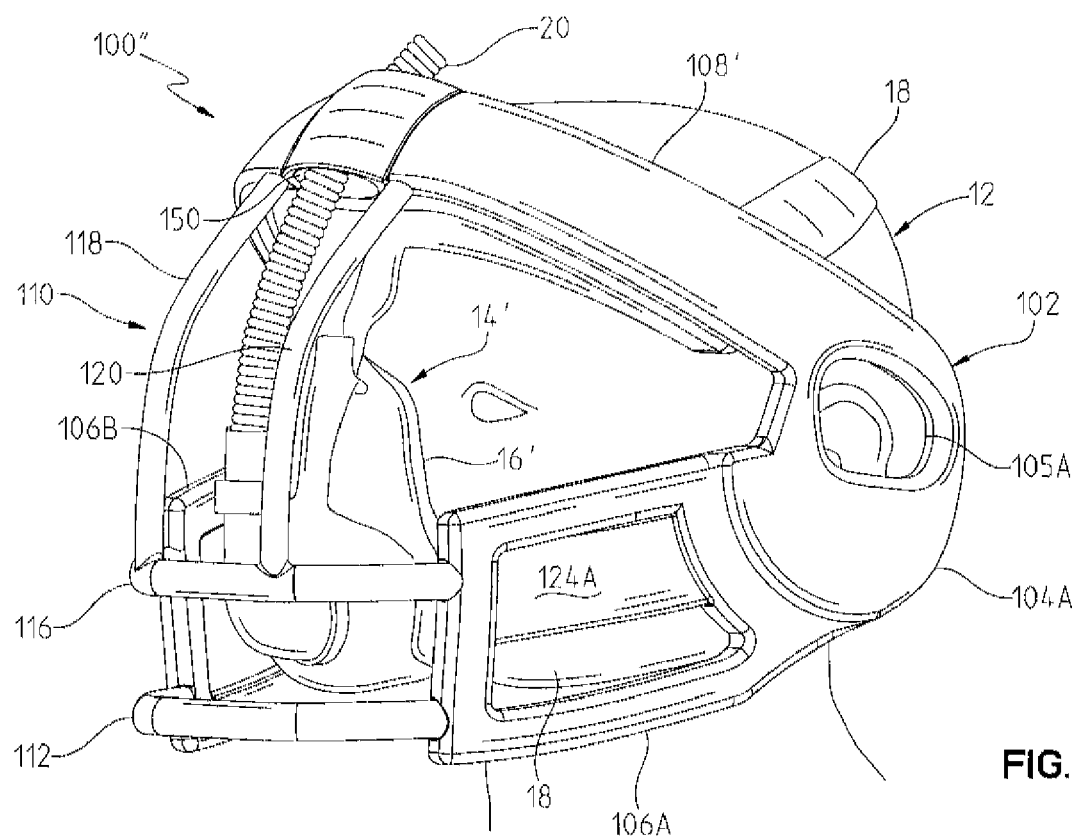
FIG. 11 is a perspective view of still illustrative embodiment of an apparatus for supporting the head of a person lying prone or on a side and wearing a breathing assist device.
Figure 12:
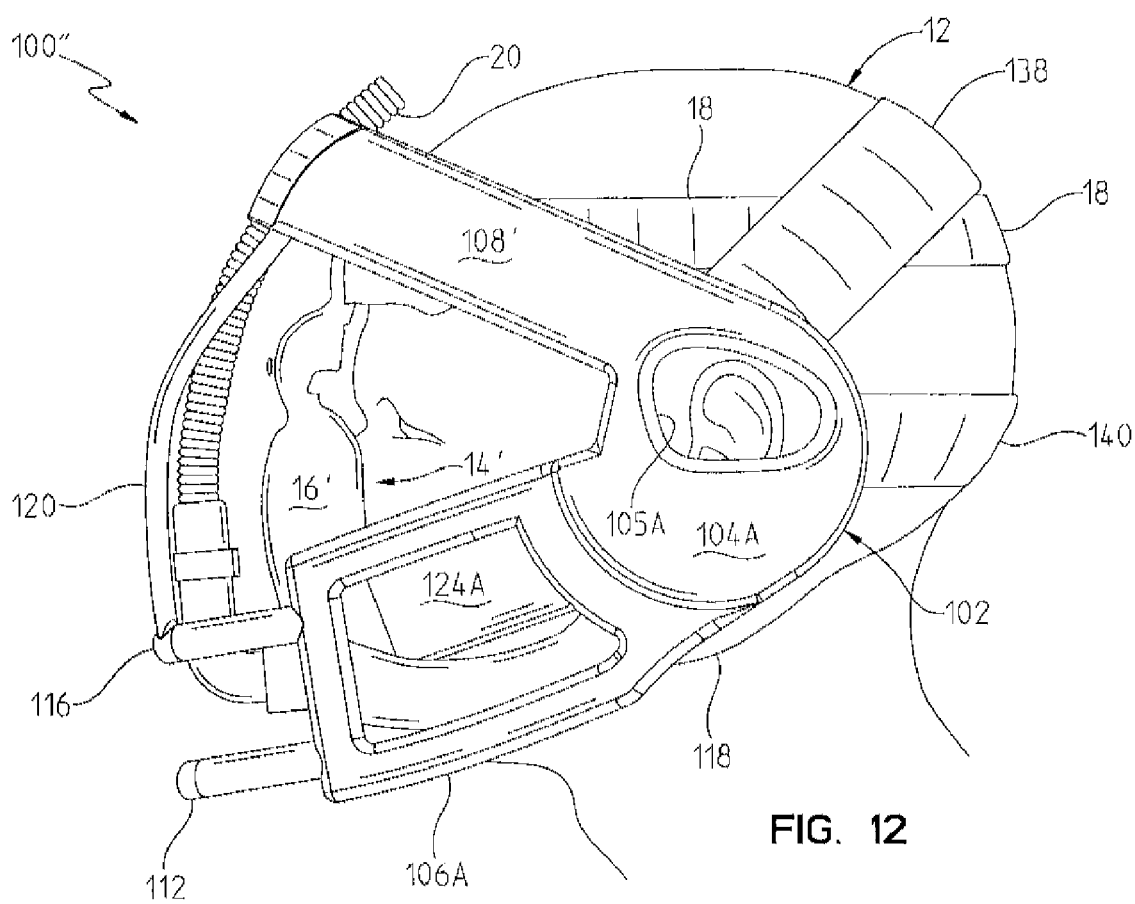
FIG. 12 is a side elevation view of the embodiment illustrated in FIG. 11.
Figure 13:
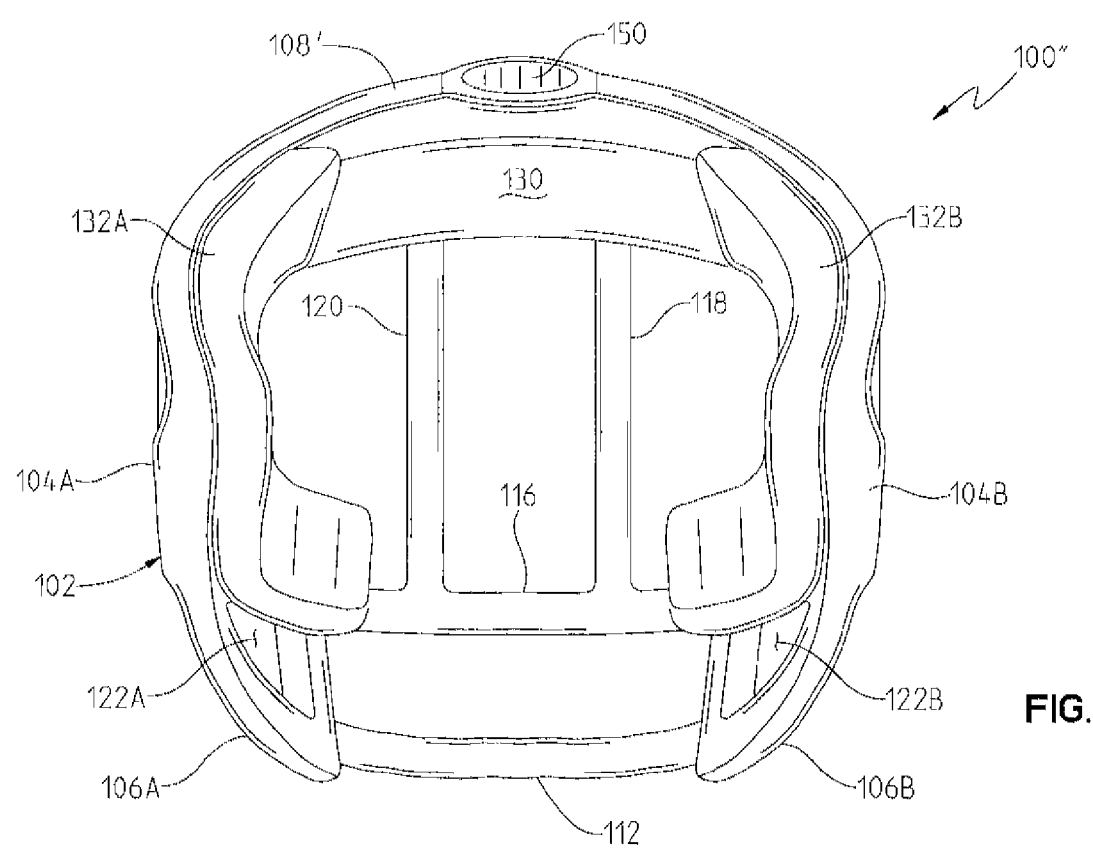
FIG. 13 is a rear view of the embodiment illustrated in FIGS. 11 and 12 showing features internal to the illustrated apparatus.

Referring now to FIGS. 11-13, another alternative embodiment of an apparatus 100" for supporting the head 12 of a person lying prone or on a side is shown. The apparatus 100" is identical in may respect to the apparatus 100 illustrated and described with respect to FIGS. 5-7 and the apparatus 100' illustrated and described with respect to FIGS. 8-10, and like numbers are therefore used to identify like components. In the illustrated embodiment, the apparatus 100" differs from the apparatus 100 and the apparatus 100' in that the apparatus 100" is intended specifically for use with a combination mouth and nose-type breathing assist device 14' having a mask 16' that fits generally over, and supplies a breathing gas to, the user's nose and mouth. In this regard, the chin and face support member 125' includes only the face support members 124A and 124B, and the chin support member 126 is omitted. In the embodiment illustrated in FIGS. 11-13, the user's head 12 is supported, when the user is wearing the apparatus 100" and lying prone, by the forehead member 108, side members 104A, 104B and the face support members 124A, 124B.

Also in the embodiment illustrated in FIGS. 11-13, the front support structure 110 and the base member 102 are cooperatively arranged to provide a space between the front support structure 110 and the face of the person wearing the apparatus 100 that is sized to receive the breathing assist device 14' therein such that the various components of the breathing assist device 14', when being worn by the user 12, are contained between the face of the user 12 and the front support structure 110, i.e., such that none of the various components of the breathing assist device 14' extend beyond the front support structure 110. This allows the person wearing the breathing assist device 14 and the apparatus 100" to lie fully prone and face-down with the front support structure 110 supported by a support surface, e.g., the surface upon which the person is lying, such as a conventional mattress or the like. It will be understood that the various alternative structures and/or omissions described above with respect to the apparatus 100 illustrated and described with respect to FIGS. 5-7 are also applicable to the apparatus 100" illustrated in FIGS. 11-13.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected. For example, while some embodiments of the apparatus illustrated and described herein are disclosed as being intended for use by patients wearing a breathing assist device and others are disclosed as being intended for use by patients not wearing a breathing assist device, it will be understood that any of the embodiments of the apparatus illustrated and described herein may be used with or without a breathing assist device. As another example, while the base members of the various embodiments of the apparatus illustrated and described herein are disclosed as being formed of a rigid or semi-rigid material, conventional padding or cushioning material may be attached to or formed integral with all or portions of the outer surface of the apparatus. As a further example, while some of the embodiments have been illustrated and described herein as being intended for use by patients wearing a breathing assist device generally, and more specifically any of a continuous positive air pressure (CPAP) device, a two-pressure positive airway pressure (BiPAP) device, a variable pressure positive airway pressure (VPAP) device and an automatic positive airway pressure (APAP) device, those skilled in the art will recognize that any of the embodiments of the apparatus illustrated and described herein may be used with, and/or easily modified to accommodate, other breathing assist devices such as a conventional endotracheal tube or other conventional breathing assist devices. Any modifications to the apparatus illustrated and described herein that may be made to accommodate any such alternate breathing assist device would be a mechanical step for a skilled artisan. The apparatus illustrated and described herein may be used by persons, in their homes, that suffer from one or more sleep disorders, by health care professionals prior to, during and/or after one or more surgical operations, by health care professionals as a form of treatment of injuries or other medical conditions or the like. It will be understood that such illustrated uses are provided only by way of example, and are not intended to limit the apparatus illustrated and described herein to any particular one or more uses.

What is claimed is:

1. An apparatus for supporting the head of a person lying prone or on a side, the apparatus comprising:
   a base member configured to be worn on the head of the person and to rotate between a plurality of positions relative to a support surface upon which the base member rests, the base member defining a first rear portion configured to extend over one ear of the person, a second rear portion configured to extend over an opposite ear of the person, a first face support portion having one end integral with the first rear portion and a opposite end extending forwardly from the first rear portion, and a second face support portion having one end integral with the second rear portion and a opposite end extending forwardly from the second rear portion, the first and second face support portions configured contact opposite sides of the face of the person, and
   a front support structure mounted to the base member, the front support structure and the base member cooperatively arranged to define a space between the front support structure and the first and second face support portions of the base member, the first and second face support portions of the base member configured to support the face of the person away from the front support structure when the person is lying prone or on a side and with the base member in any of the plurality of positions,
   wherein the opposite ends of the first and second face support portions each define one of a terminal end of a respective one of the first and second face support portions and an integral chin support member extending between the first and second support portions.

2. The apparatus of claim 1 wherein the space defined between the front support structure and the face of the person wearing the apparatus is sized to provide for adequate ventilation when the person wearing the apparatus is lying fully prone and face-down with the front support structure supported by the support surface.

3. The apparatus of claim 2 wherein the base member comprises a forehead support member integral with and extending between the first and second rear portions of the base member, the forehead support member configured to receive and support at least a portion of a forehead of the person.

4. The apparatus of claim 3 wherein the base member comprises:
the chin support member, the chin support member integral with and extending between the opposite ends of the first and second face support portions of the base member, the chin support member
configured to receive and support at least a portion of a chin of the person.

5. The apparatus of claim 4 further comprising a securing member configured to extend between the first and second rear portions of the base member and to secure the apparatus to the person's head.

6. The apparatus of claim 1 wherein the base member is configured to be worn by a person that is also wearing a breathing assist device,
and wherein the space defined between the front support structure and the face of the person wearing the apparatus is sized to receive the breathing assist device therein such that components of the breathing assist device are substantially contained between the face of the user and the front support structure.

7. The apparatus of claim 6 wherein the breathing assist device comprises a mask fluidly connected to one end of a gas line,
and wherein the base member defines an opening through which the gas line extends externally to the base member.

8. The apparatus of claim 7 wherein the breathing assist device further comprises a source of gas,
and wherein an opposite end of the gas line is configured to be fluidly connectable to the source of gas.

9. The apparatus of claim 8 wherein the source of gas is an air pump.

10. The apparatus of claim 7 wherein the mask of the breathing assist device comprises a nasal mask configured to provide a breathing gas to a nose of the person wearing the breathing assist device.

11. The apparatus of claim 7 wherein the base member comprises a forehead support member extending between the first and second rear portions of the base member, the forehead support member configured to receive and support at least a portion of a forehead of the person, and
wherein the opening through which the gas line extends is defined through the forehead support member such that the gas lines extends from within the space, through the opening and externally to the base member.

12. The apparatus of claim 6 wherein the base member comprises:
the chin support member, the chin support member integral with and extending between the opposite ends of the first and second face support portions of the base member, the chin support member
configured to receive and support at least a portion of a chin of the person.

13. The apparatus of claim 7 wherein the mask of the breathing assist device comprises a face mask configured to provide a breathing gas to a nose and mouth of the person wearing the breathing assist device.

14. The apparatus of claim 6 wherein the breathing assist device comprises one of a continuous positive air pressure (CPAP) device, a two-pressure positive airway pressure (Bi-PAP) device, a variable pressure positive airway pressure (VPAP) device and an automatic positive airway pressure (APAP) device.

15. The apparatus of claim 1 further comprising at least one strap attached to the base member and configured to engage the head of the person wearing the apparatus, the at least one strap configured to restrain movement of the apparatus relative to the user's head.

16. The apparatus of claim 15 wherein the at least one strap comprises a first strap having one end attached to the first rear portion of the base member and a second strap having one end attached to the second rear portion of the base member, and further comprising a retaining structure configured to releasably engage opposite ends of the first and second straps.

17. The apparatus of claim 1 wherein the opposite end of the first face support portion of the base member defines the terminal end of the first face support portion and the opposite end of the second face support portion of the base member defines the terminal end of the second face support portion.

18. The apparatus of claim 1 wherein the base member defines a first side portion extending forwardly from the first rear portion of the base member to a terminal end of the first side portion and a second side portion extending forwardly from the second rear portion of the base member to a terminal end of the second side portion, the first and second side portions configured to extend along opposite sides of the face of the person with the first face support portion between the first side portion and the face of the person and with the second face support portion between the second side portion and the face of the person,
and wherein the front support member is attached to the terminal ends of each of the first and second side portions.

19. The apparatus of claim 18 wherein the base member comprises a forehead support member extending between the first and second rear portions of the base member, the forehead support member configured to receive and support at least a portion of a forehead of the person,
and wherein the front support structure comprises:
at least a first support member having one end attached to the terminal end of the first side portion and an opposite end attached to the terminal end of the second side portion, and
at least a second support member having one end attached to the at least a first support member and an opposite end attached to the forehead support member.

20. The apparatus of claim 19 wherein the at least a first support member comprises a pair of parallel tubes each having one end attached to the terminal end of the first side portion and an opposite end attached to the terminal end of the second side portion,
and wherein the at least a second support member comprises a pair of parallel tube each having one end attached to one of the parallel tubes comprising the first support member and an opposite end attached to the forehead support member.

* * * * *